(12) United States Patent
Sinha et al.

(10) Patent No.: US 8,426,454 B2
(45) Date of Patent: Apr. 23, 2013

(54) THERAPEUTIC COMPOUNDS

(75) Inventors: Santosh C. Sinha, Ladera Ranch, CA (US); Smita S. Bhat, Irvine, CA (US); Todd M. Heidelbaugh, Fountain Valley, CA (US); Daniel W. Gil, Corona Del Mar, CA (US); Ken Chow, Newport Coast, CA (US); Michael E. Garst, Newport Coast, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/673,351

(22) PCT Filed: Aug. 14, 2008

(86) PCT No.: PCT/US2008/073110
§ 371 (c)(1),
(2), (4) Date: Apr. 6, 2011

(87) PCT Pub. No.: WO2009/023758
PCT Pub. Date: Feb. 19, 2009

(65) Prior Publication Data
US 2011/0178144 A1    Jul. 21, 2011

Related U.S. Application Data

(60) Provisional application No. 60/955,972, filed on Aug. 15, 2007.

(51) Int. Cl.
*A61K 31/421*   (2006.01)
*A61K 31/426*   (2006.01)
*A61K 31/4168*   (2006.01)
*C07D 233/02*   (2006.01)
*C07D 263/04*   (2006.01)
*C07D 277/04*   (2006.01)

(52) U.S. Cl.
USPC ........ 514/370; 548/190; 548/234; 548/326.5; 514/377; 514/386

(58) Field of Classification Search .................. 548/190, 548/234, 326.5; 514/370, 377, 386
See application file for complete search history.

(56) References Cited

U.S. PATENT DOCUMENTS

| | | | |
|---|---|---|---|
| 2,870,161 A | 1/1959 | Bloom | |
| 2,883,410 A | 1/1959 | Bloom | |
| 4,861,789 A * | 8/1989 | Berge et al. | 514/370 |
| 7,141,597 B2 | 11/2006 | Chow | |

FOREIGN PATENT DOCUMENTS

| | | |
|---|---|---|
| DE | 1963192 | 6/1971 |
| JP | 62267270 | 11/1987 |
| WO | WO2007020377 | 2/2007 |

OTHER PUBLICATIONS

CAS abstract of Wong et al, Bioorganic & Medicinal Chem. Letters (1994), vol. 4(19), pp. 2317-2322.*
Prodrugs and Drug Delivery Systems, which is a chapter in Richard B. Silverman, Organic Chemistry of Drug Design and Drug Action, 2d Ed., Elsevier Academic Press: Amsterdam, 2004, pp. 496-557.

* cited by examiner

*Primary Examiner* — Kamal Saeed
*Assistant Examiner* — Janet L Coppins
(74) *Attorney, Agent, or Firm* — Kevin J. Forrestal

(57) ABSTRACT

Disclosed herein is a compound having a structure

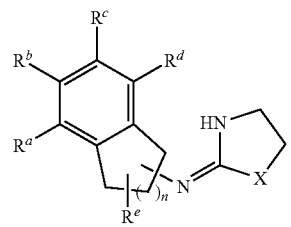

compositions, methods, and medicaments related thereto are also disclosed.

12 Claims, No Drawings

THERAPEUTIC COMPOUNDS

CROSS REFERENCE TO RELATED APPLICATIONS

This is a national stage application under 35 U.S.C. §371 of PCT patent application PCT/US2008/073110, filed on Aug. 14, 2008, which claims the benefit of U.S. Provisional Patent Application 60/955,972, filed Aug. 15, 2007, each of which is hereby incorporated by reference in its entirety.

BACKGROUND OF THE INVENTION

There is a continuing need for alpha adrenergic compounds for treating pain, glaucoma and other conditions.

DESCRIPTION OF THE INVENTION

Disclosed herein is a compound having a structure

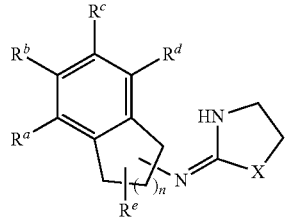

wherein X is O, S, or NH;
n is 2 or 3;
$R^a$, $R^b$, $R^c$, and $R^d$ are stable moieties independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms; and
$R^e$ is H or $C_{1-4}$ alkyl.

These compounds are useful for the treatment of pain, glaucoma, and the reduction of intraocular pressure. The compound is incorporated into a dosage form or a medicament and administered to the mammal in need thereof. For example, a liquid composition may be administered as an eye drop for the treatment of glaucoma or lowering intraocular pressure. A solid dosage form may also be administered orally for any of these conditions. Other types of dosage forms and medicaments are well known in the art, and may also be used here.

For the purposes of this disclosure, "treat," "treating," or "treatment" refer to the use of a compound, composition, therapeutically active agent, or drug in the diagnosis, cure, mitigation, treatment, prevention of disease or other undesirable condition.

Unless otherwise indicated, reference to a compound should be construed broadly to include pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. While not intending to limit the scope of the invention, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion. Examples of tautomers are depicted below.

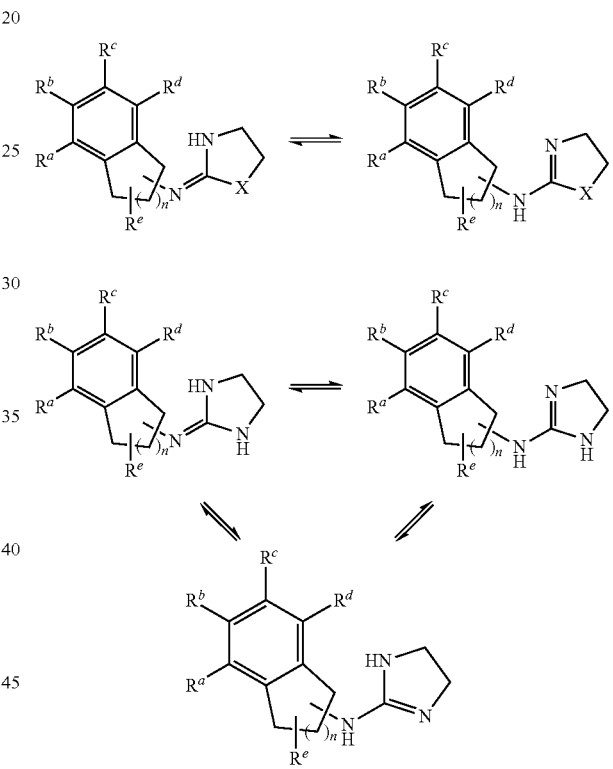

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

X is O, S, or NH. Thus, compounds of any of the structures depicted below are contemplated.

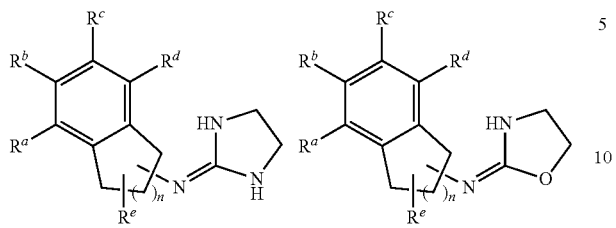

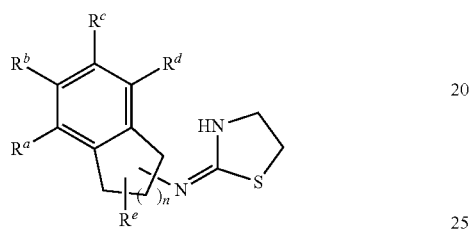

Since n is 2 or 3, compounds according to either of the structures depicted below are contemplated.

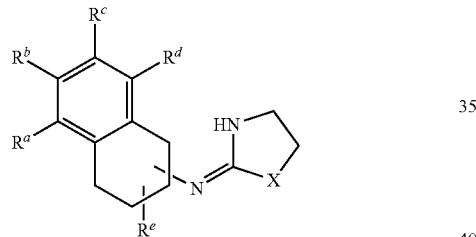

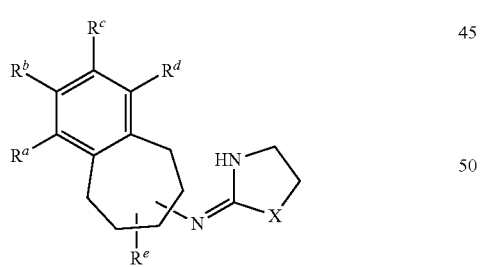

The part of the compound:

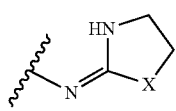

attaches to one of the non-aromatic carbons of the ring system. In other words, the compounds having the structures depicted below are contemplated.

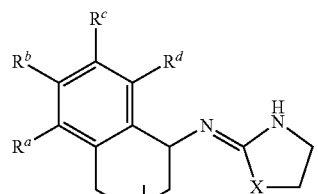

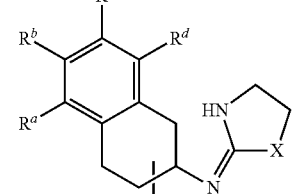

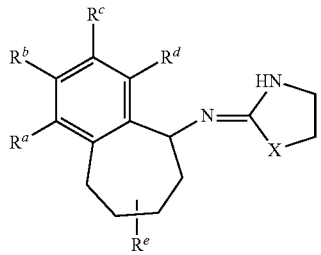

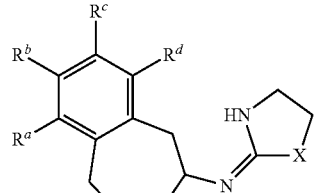

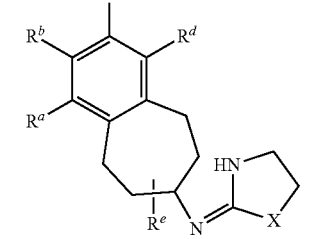

$R^a$, $R^b$, $R^c$, and $R^d$ are stable moieties independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms.

Subject to the constraints described herein (e.g. limits on the number of atoms), examples of $R^a$, $R^b$, $R^c$, and $R^d$ include, but are not limited to:

Hydrocarbyl, meaning a moiety consisting of carbon and hydrogen only, including, but not limited to:
  a. alkyl, meaning hydrocarbyl having no double or triple bonds, including, but not limited to:
     linear alkyl, e.g. methyl, ethyl, n-propyl, n-butyl, etc.,
     branched alkyl, e.g. iso-propyl, t-butyl and other branched butyl isomers, etc.,
     cycloalkyl, e.g. cyclopropyl, cyclobutyl, etc.,
     combinations of linear, branched, and/or cycloalkyl;
  alkenyl, e.g. hydrocarbyl having 1 or more double bonds, including linear, branched, or cycloalkenyl c. alkynyl, e.g. hydrocarbyl having 1 or more triple bonds, including linear, branched, or cycloalkynyl;

d. combinations of alkyl, alkenyl, and/or akynyl alkyl-CN, such as —$CH_2$—CN, —$(CH_2)_2$—CN; —$(CH_2)_3$—CN, and the like;

hydroxyalkyl, i.e. alkyl-OH, such as hydroxymethyl, hydroxyethyl, and the like;

ether substituents, including —O-alkyl, alkyl-O-alkyl, and the like;

thioether substituents, including —S-alkyl, alkyl-S-alkyl, and the like;

amine substituents, including —$NH_2$, —NH-alkyl, —N-alkyl$^1$alkyl$^2$ (i.e., alkyl$^1$ and alkyl$^2$ are the same or different, and both are attached to N), alkyl-$NH_2$, alkyl-NH-alkyl, alkyl-N-alkyl$^1$alkyl$^2$, and the like;

aminoalkyl, meaning alkyl-amine, such as aminomethyl (—$CH_2$-amine), aminoethyl, and the like;

ester substituents, including —$CO_2$-alkyl, —$CO_2$-phenyl, etc.;

other carbonyl substituents, including aldehydes; ketones, such as acyl (i.e.

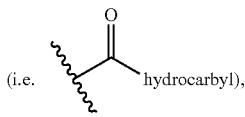

and the like; in particular, acetyl, propionyl, and benzoyl substituents are contemplated;

fluorocarbons or hydrofluorocarbons such as —$CF_3$, —$CH_2CF_3$, etc.; and

—CN;

combinations of the above are also possible, subject to the constraints defined;

Alternatively, a substituent may be —F, —Cl, —Br, or —I.

In particular, alkyl having from 1 to 4 carbon atoms is contemplated;

$R^a$, $R^b$, $R^c$, and $R^d$ stable, i.e. they must be stable enough to be stored in a bottle at room temperature under a normal atmosphere for at least 12 hours, or stable enough to be useful for any purpose disclosed herein.

If $R^a$, $R^b$, $R^c$, or $R^d$ is a salt, for example of a carboxylic acid or an amine, the counter-ion of said salt, i.e. the ion that is not covalently bonded to the remainder of the molecule is not counted for the purposes of the number of atoms in the moiety. Thus, for example, the salt —$CO_2^-Na^+$ consists of 1 carbon and 2 oxygen atoms, i.e. sodium is not counted. In another example, the salt —$NH(Me)_2^+Cl^-$ consists of 2 carbon atoms, 1 nitrogen atom, and 7 hydrogen atoms, i.e. chlorine is not counted.

In another embodiment, $R^a$, $R^b$, $R^c$, and $R^d$ are independently —H, alkyl having from 1 to 4 carbon atoms, —F, —Cl, —Br, —$CH_2OH$, an amine having from 0 to 4 carbon atoms, —$CH_2CN$, —$CF_3$, or acyl having from 1 to 4 carbon atoms.

In another embodiment, $R^a$, $R^b$, $R^c$, and $R^d$ are independently —H, —F, —Cl, —Br, —$CH_3$, —$NHCH_3$, or —$CF_3$.

$R^e$ is H or $C_{1-4}$ alkyl, i.e. methyl, ethyl, n-propyl, isopropyl, and the butyl isomers. $R^e$ attaches to one of the non-aromatic carbons of the ring system. Thus, compounds having any of the structures depicted below are contemplated.

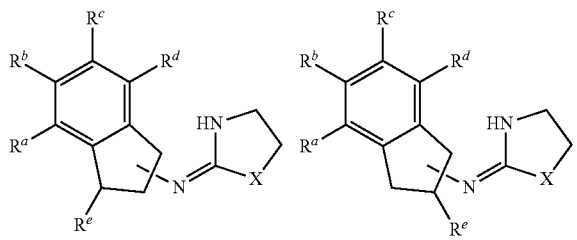

In one embodiment n is 2.
In another embodiment n is 3.
In another embodiment X is O.
In another embodiment X is S.
In another embodiment X is NH.
In another embodiment $R^a$, $R^b$, $R^c$, and $R^d$ are independently selected from H, methyl, ethyl, $C_3$ alkyl, and $C_4$ alkyl, F, Cl, Br, —$CH_2OH$, —$CH_2NH_2$, —$CHNH(C_{1-4}$ alkyl), —$CN(C_{1-4}$ alkyl$)_2$, —$CH_2CN$, and $CF_3$.
In another embodiment $R^a$, $R^b$, $R^c$, and $R^d$ are independently selected from H, methyl, ethyl, F, Cl, Br, —$CH_2CN$, and $CF_3$.
In another embodiment $R^e$ is H.
In another embodiment $R^e$ is methyl.
In another embodiment, the compound has a structure

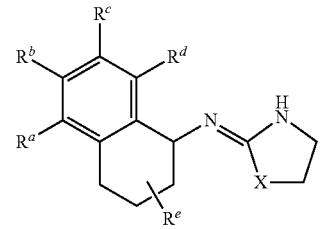

Another embodiment is method of reducing intraocular pressure comprising administering a compound disclosed herein to a mammal in need thereof.

Another embodiment is method of treating pain comprising administering a compound disclosed herein to a mammal in need thereof.

Some hypothetical examples of useful compounds are shown below.

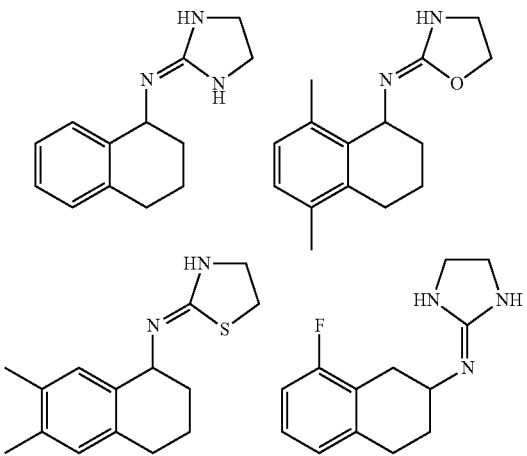

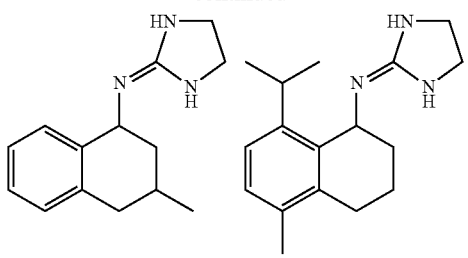
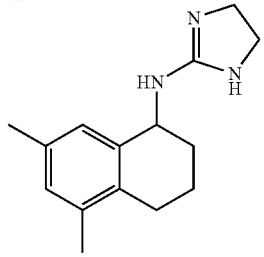

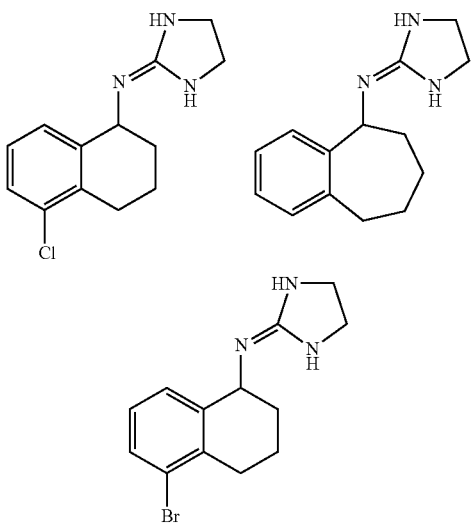

Other useful compounds include:
(4,5-Dihydro-1H-imidazol-2-yl)-(1,2,3,4-tetrahydro-naphthalen-1-yl)amine,
[(1S)-(4,5-Dihydro-1H-imidazol-2-yl)-(1,2,3,4-tetrahydro-naphthalen-1-yl)]amine, and
(4,5-Dihydro-1H-imidazol-2-yl)-(5,7-dimethyl-1,2,3,4-tetrahydro-naphthalen-1-yl)-amine.

Synthetic Methods

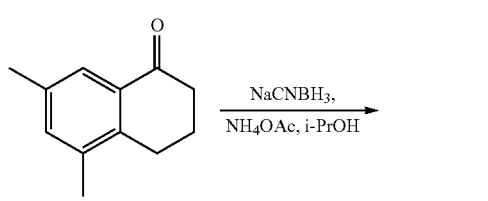
Intermediate 4

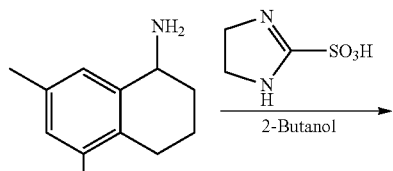
Intermediate 5

Intermediate 6
904

A solution of 5,7-dimethyl-3,4-dihydro-2H-naphthalen-1-one (commercially available, 12.3 g, 28.3 mmol)-(Intermediate 4) in isopropanol (100 mL) was treated with sodium cyanoborohydride (9.01 g, 143.5 mmol) and ammonium acetate (47.4 g, 615 mmol), and the reaction mixture was refluxed for 16 hours. The mixture was basified with sodium hydroxide (10 mL). The residue was isolated in a typical aqueous workup to give (6.5 g, 37.1 mmol) (Intermediate 5). A mixture of (500 mg, 5.7 mmol) (Intermediate 5) and 4,5-dihydro-1H-imidazole-2-sulfonic acid (940 mg, 6.3 mmol) in 2-butanol (30 mL) was refluxed for 24 h. The mixture was evaporated under reduced pressure. This material was purified by chromatography on silica gel with 5% $NH_3$-MeOH:$CH_2Cl_2$ to give (90 mg, 3.7 mmol, 36%) of (4,5-dihydro-1H-imidazol-2-yl)-(5,7-dimethyl-1,2,3,4-tetrahydro-naphthalen-1-yl)-amine (904).

Following a procedure similar to that for 904 afforded the following compounds.

(4,5-Dihydro-1H-imidazol-2-yl)-(1,2,3,4-tetrahydro-naphthalen-1-yl)amine, 639:
$^1$HNMR ($CD_3OD$, 300 MHz): δ=7.26-7.14 (m, 4H), 4.65 (t, J=6.0 Hz, 1H), 3.74 (s, 4H), 2.65-2.90 (m, 2H), 1.86-2.08 (m, 3H), 1.42-1.47 (m, 1H).

[(1S (4,5-Dihydro-1H-imidazol-2-yl)-(1,2,3,4-tetrahydro-naphthalen-1-yl)]amine, 323:
$^1$HNMR ($CD_3OD$, 500 MHz): δ=7.06-7.37 (m, 4H), 4.65 (t, J=5.0 Hz, 1H), 3.74 (s, 4H), 2.72-2.98 (m, 2H), 1.77-2.23 (m, 3H), 1.44-1.48 (m, 1H).

(4,5-Dihydro-1H-imidazol-2-yl)-(5,7-dimethyl-1,2,3,4-tetrahydro-naphthalen-1-yl)-amine, 904:
$^1$HNMR ($CD_3OD$, 500 MHz): δ=6.94 (d, 2H), 4.61-4.67 (m, 1H), 3.90 (s, 4H), 2.63-2.60 (m, 2H), 1.82-1.98 (m, 4H), 2.28 (s, 3H), 2.28 (s, 3H).

Biological Data

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

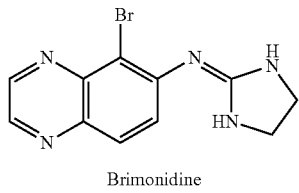 [SMILES: Brc1c(N=C2NCCN2)ccc2nccnc12]

Brimonidine

The results of the RSAT assay with several exemplary compounds of the invention are disclosed in Table 1 above together with the chemical formulas of these exemplary compounds. EC$_{50}$ values are nanomolar. ND stands for "not determinable" at concentrations less than 10 micromolar. IA stands for "intrinsic activity."

TABLE 1

| Structure | Alpha 2B | Alpha 2C | Alpha 2A |
|---|---|---|---|
| 639 | 37 (84) | 179 (50) | nd (25) |
| 323 | 49 (102) | 308 (42) | nd (12) |

TABLE 1-continued

| Structure | Alpha 2B | Alpha 2C | Alpha 2A |
|---|---|---|---|
| 904 | 68 (80) | nd (4) | 1622 (35) |

Methods of formulating these compounds are well known in the art. For example, U.S. Pat. No. 7,141,597 (especially column 10, line 27 to column 14, line 47) contains information that may be used for general guidance. Similar relevant information is also available in numerous other sources. The biological activity of the compounds disclosed herein (e.g. Table 1) may be used for additional general guidance on dosage, depending on the particular use of a compound.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound having a structure

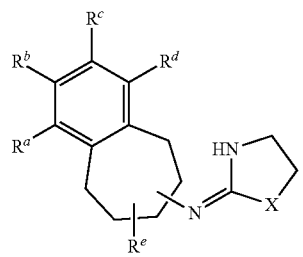

wherein X is O, S, or NH;
R$^a$, R$^b$, R$^c$, and R$^d$ are stable moieties independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms; and
R$^e$ is H or C$_{1-4}$ alkyl.

2. The compound of claim 1 wherein X is O.
3. The compound of claim 1 wherein X is S.
4. The compound of claim 1 wherein X is NH.
5. The compound of claim 1 wherein R$^a$, R$^b$, R$^c$, and R$^d$ are independently selected from H, methyl, ethyl, C$_3$ alkyl, and C$_4$ alkyl, F, Cl, Br, —CH$_2$OH, —CH$_2$NH$_2$, —CHNH(C$_{1-4}$ alkyl), —CN(C$_{1-4}$ alkyl)$_2$, —CH$_2$CN, and CF$_3$.

6. The compound of claim 1 wherein $R^a$, $R^b$, $R^c$, and $R^d$ are independently selected from H, methyl, ethyl, F, Cl, Br, —$CH_2CN$, and $CF_3$.

7. The compound of claim 5 wherein $R^e$ is H.

8. The compound of claim 5 wherein $R^e$ is methyl.

9. A method of treating pain comprising administering a compound having a structure

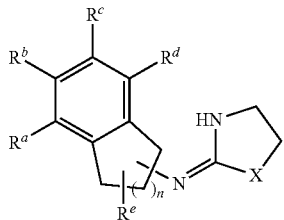

wherein X is O, S, or NH;
n is 2 or 3;
$R^a$, $R^b$, $R^c$, and $R^d$ are stable moieties independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms; and $R^e$ is H or $C_{1-4}$ alkyl,
to a mammal in need thereof.

10. The method of claim 9 wherein the compound is selected from (4,5-Dihydro-1H-imidazol-2-yl)-(1,2,3,4-tetrahydro-naphthalen-1-yl) amine, [(1S)-(4,5-Dihydro-1H-imidazol-2-yl)-(1,2,3,4-tetrahydro-naphthalen-1-yl)] amine, and (4,5-Dihydro-1H-imidazol-2-yl)-(5,7-dimethyl-1,2,3,4-tetrahydro-naphthalen-1-yl)-amine.

11. A method of reducing intraocular pressure comprising administering a compound of claim 1 to a mammal in need thereof.

12. The method of claim 9 having a structure

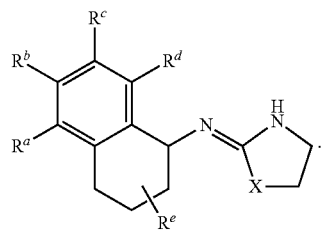

* * * * *